(12) United States Patent
Hartle et al.

(10) Patent No.: US 7,946,155 B2
(45) Date of Patent: May 24, 2011

(54) METHOD FOR QUANTITATIVELY DETERMINING UNBOUND METAL IN FORMULATIONS CONTAINING CHELATES

(75) Inventors: Jennifer W. Hartle, Harrisville, UT (US); R. Charles Thompson, Morgan, UT (US)

(73) Assignee: Albion Laboratories, Inc., Clearfield, UT (US)

( * ) Notice: Subject to any disclaimer, the term of this patent is extended or adjusted under 35 U.S.C. 154(b) by 462 days.

(21) Appl. No.: 12/181,874

(22) Filed: Jul. 29, 2008

(65) Prior Publication Data

US 2009/0071232 A1    Mar. 19, 2009

Related U.S. Application Data

(60) Provisional application No. 60/973,653, filed on Sep. 19, 2007.

(51) Int. Cl.
*G01N 33/20* (2006.01)
(52) U.S. Cl. ................. 73/61.42; 73/53.01
(58) Field of Classification Search .......... 73/53.01, 73/61.41, 61.42
See application file for complete search history.

(56) References Cited

U.S. PATENT DOCUMENTS

| | | | | |
|---|---|---|---|---|
| 3,630,681 | A * | 12/1971 | Arikawa | 436/90 |
| 3,763,136 | A * | 10/1973 | Huber et al. | 530/401 |
| 3,926,559 | A * | 12/1975 | Stevens | 436/79 |
| 5,459,040 | A * | 10/1995 | Hammock et al. | 435/7.1 |
| 5,583,219 | A * | 12/1996 | Subramanian et al. | 540/465 |
| 5,922,302 | A * | 7/1999 | Goldenberg et al. | 424/1.41 |
| 6,127,189 | A | 10/2000 | Joullie et al. | |
| 6,475,743 | B1 * | 11/2002 | Bar-Or et al. | 435/7.1 |
| 7,144,737 | B2 | 12/2006 | Hartle et al. | |
| 2003/0023037 | A1 * | 1/2003 | Tchaga | 530/350 |
| 2003/0226755 | A1 * | 12/2003 | Ramsey | 204/600 |
| 2006/0292698 | A1 | 12/2006 | Hartle et al. | |
| 2008/0248583 | A1 | 10/2008 | Ericson et al. | |

FOREIGN PATENT DOCUMENTS

| | | | |
|---|---|---|---|
| JP | 60-235057 A | * | 11/1985 |
| JP | 1-113652 | * | 5/1989 |
| JP | 3-54458 A | * | 3/1991 |
| WO | WO 2006/034195 A2 | | 3/2006 |

OTHER PUBLICATIONS

Ericson, C., Ashmead, S.D., *A Novel Approach in Confirming Dietary Amino Acid Chelates by Utilization of Ninhydrin*, AOAC 118th International meeting, 1 page (2004).

Derebe, M.G., et al., "Synthesis and Characterization of Some Metal Complexes of a Schiff Base Derived from Ninhydrin and α,L-Alanine," 16(1) *Bull. Chem. Soc. Ethiop.* 53-64 (2002).

Gupta, D. et al., "Kinetics and Mechanism of Ninhydrin Reaction with Copper(II) Complexes of Glycine and α-Alanine, Elucidation of the Template Mechanism," 25 *International Journal of Chemical Kinetics* 437-443 (1993).

Hassan, A., "Some Metal Complexes of Schiff Base Ligands Derived from Ninhydrin and Some Amino Acids," 27(6) *Synth. React. Inorg. Met.-Org. Chem.* 855-861 (1997).

Jeppsen, R.B., "Mineral Supplementation in Plants Via Amino Acid Chelation," 445 *ACS Symposium Series* 320-331 (1991).

Kabir-Ud-Din, et al., "Micellar Effects on the Rates of Condensation Reaction Between Copper(II)-Histidine Complex and Ninhydrin," 31 *International Journal of Chemical Kinetics* 729-736 (1999).

Khan, Z., et al., "Template Mechanism and Kinetics for the Complexation of Ninhydrin with Copper(II) Complexes of Asparagine and Serine," 28 *International Journal of Chemical Kinetics* 893-897 (1996).

Khan, Z., et al., "Template Mechanism for the Internation of Ninhydrin with Cadmium(II) and Copper(II) Complexes of L-aspartic acid—A Kinetic Study," 33A *Indian Journal of Chemistry* 735-739 (1994).

Krauss, A., "Staining of Amino Acids with Metal Salt-Ninhydrin Mixtures," 229(5) *Fresenius' Zeitschrift fuer Analytische Chemie* 343-350 (1967).

Lennard, C.J., et al., "Synthesis and Evaluation of Ninhydrin Analogues as Reagents for the Development of Latent Fingerprints on Paper Surfaces," 28 *Journal of the Forensic Science Society* 3-23 (1988).

Menzel, E.R., et al., "Fluorescent Metal-Ruhemann's Purple Coordination Compounds: Applications to Latent Fingerprint Detection," 35(1) *Journal of Forensic Sciences* 25-34 (Jan. 1990).

Moffat, E.D., et al., "Polychromatic Technique for the Identification of Amino Acids on Paper Chromatograms," 31(5) *Analytical Chemistry* 926-928 (May 1959).

Rao, N., et al., "Studies on the Synthesis, Characterisation and Antimicrobial Activity of New Co(II), Ni(II) and Zn(II) Complexes of Schiff Base Derived from Ninhydrin and Glycine," 3 *Biol. Metals* 19-23 (1990).

Szczepaniak, W., et al., "Extraction Study of Alkali Metal (2.2.2) Cryptates with Complex Anion Co(PAR)2-," 32 *Chemia Analityczna* 787-795 (1987).

Singh, J.V., et al., "Effect of Manganese on Ninhydrin Color Development by Amino Acids," 85(2) *Analytical Biochemistry* 581-585 (1978).

Singh, S.P., et al., "Reactions of Fulvic Acid Complexes of Zn and Cu with Alka Line Soils," 33(6) *Agrochimica* 434-440 (1989). Skoog, D.A., et al., Chapter 27: Selected Methods of Analysis, Fundamentals of Analytical Chemistry, 7th edition, Saunders College Publishing, New York, pp. 721-773, specifically p. 723 (1996).

* cited by examiner

Primary Examiner — Daniel S Larkin
(74) Attorney, Agent, or Firm — Ryan L. Marshall; Brinks Hofer Gilson & Lione

(57) ABSTRACT

Methods are provided for quantitatively determining the amount of unbound metal present in a sample suspected of containing a metal-ligand chelate.

17 Claims, No Drawings

US 7,946,155 B2

METHOD FOR QUANTITATIVELY DETERMINING UNBOUND METAL IN FORMULATIONS CONTAINING CHELATES

CROSS REFERENCE TO RELATED APPLICATION

This application claims the benefit under 35 U.S.C. §119 (e) of U.S. Provisional Patent Application No. 60/973,653, filed Sep. 19, 2007, which is incorporated, in its entirety, by this reference.

TECHNICAL FIELD OF THE INVENTION

The present invention relates to methods that can be used to quantitatively measure the amount of unbound metal in metal-chelate formulations.

BACKGROUND OF THE INVENTION

Chelates are generally produced by the reaction or association of a ligand with a metal cation, resulting in a complex. Amino acid chelates may be made by the reaction of an α-amino acid and metal ion typically, but not necessarily, having a valence of two or more to form a ring structure. In such a reaction, the positive electrical charge of the metal ion is neutralized or delocalized by the electrons available through the carboxylate and or free amino groups of the α-amino acid. The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.

One advantage of using amino acid chelates in the field of mineral nutrition is that they are readily absorbed in the gut and mucosal cells by means of active transport. Chelates enable minerals to be absorbed in biological processes along with amino acids as a single unit utilizing the amino acids as carrier molecules. Therefore, the problems associated with the competition of ions for active sites and the suppression of specific nutritive mineral elements by others can be avoided. Controlled delivery of nutritional minerals is advantageous because large quantities of those minerals often cause nausea and other discomforts as well as create an undesirable taste.

Since metal amino acid chelates serve as a delivery means for mineral supplements in the fields of plant nutrition, animal feed, and human nutritional supplements, there is a growing need for methods of characterizing chelates, and particularly quantitative assessment of bound and unbound metal amounts in formulations. The use of spectroscopic means, such as Fourier Transform infrared spectroscopy (FTIR), to characterize chelates is limited. Such techniques are sensitive to water present in the sample, and therefore, make it difficult or impossible to determine the amount of unbound metal in solution for a metal chelate. A technique that can quantify the amount of unbound metal, in chelate formulations, particularly in solution, is highly desirable since that technique could be used in the agricultural and nutritional supplement industries to attain reliable measures for comparisons and standards of formulary products and ingredients.

SUMMARY OF THE INVENTION

The present invention generally relates to methods for assaying an amount of unbound metal in a liquid sample suspected of containing a metal-ligand chelate, comprising: contacting the sample with a liquid carrier; eluting the sample and liquid carrier through an ion chromatography column to produce an eluent; and determining the amount of unbound metal in the eluent.

The amount of unbound metal in the eluent may be determined by spectroscopic methods or by non-spectroscopic methods.

In some embodiments, the liquid carrier includes a monovalent cation buffer solution. In some embodiments, the liquid carrier has a pH of from about 2 to about 10. In some embodiments, the ion chromatography column is a cation exchange column.

In some embodiments, the metal is selected from the group consisting of: boron, calcium, chromium, cobalt, copper, iron, magnesium, manganese, potassium, selenium, vanadium and zinc, and the ligand is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

DETAILED DESCRIPTION OF THE INVENTION

Unless defined otherwise, technical and scientific terms used herein have the same meaning as commonly understood by one of ordinary skill in the art to which this invention belongs. Units, prefixes, and symbols may be denoted in their Si accepted form. Unless otherwise indicated. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. One skilled in the art will recognize many methods and materials similar or equivalent to those described herein, which could be used in the practice of the present invention. The present invention is in no way limited to the methods and materials described. For purposes of the present invention, the following terms are defined below.

The term "chelate" as used herein means a molecular entity made up of a central metal associated with at least one bidentate ligand and optionally associated with one or more mono- or multi-dentate ligands. In the interaction between the central metal and any of the ligands, the bonds between the ligand and the central metal can include covalent bonds, ionic bonds, and/or coordinate covalent bonds.

As applied in the field of mineral nutrition, there are at least two chelated products which are commercially utilized. The first is referred to as a "metal proteinate." The American Association of Feed Control Officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc. These metal proteinates also include at least one chelate ring.

Proteinates can be formed using dipeptides, tripeptides, tetrapeptides, polypeptides. Larger ligands have a molecular weight that is too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula $[C(O)CHR_1NH]_gH$ will replace one of the hydrogens attached to the nitrogen atom in Formula 1. $R_1$, as defined in Formula 1, can be H, or the residue of any other naturally occurring amino acid and g can be an integer of 1, 2 or 3. When g is 1 the ligand will be a dipeptide, when g is 2 the ligand will be a tripeptide and so forth. Amino acid chelates can also include cyclic peptides ligands such as those peptides which can act as cryptands.

An "amino acid chelate" as used herein means the product resulting from the reaction of a metal or metal ion from a soluble metal salt with one or more amino acids having a mole ratio of from 1:1 to 1:4, or, in particular embodiments, having a mole ratio 1:2, moles of metal to moles of amino acids, to form coordinate covalent bonds. The average weight of the hydrolyzed amino acids is approximately 150 and the resulting molecular weight of the chelate will typically not exceed a molecular weight of about 800 amu and more frequently less than about 1000 amu. The chelate products can be identified by the specific metal forming the chelate (e.g., iron amino acid chelate, copper amino acid chelate, etc.) An amino acid chelate may be represented at a ligand to metal molar ratio of 2:1 according to Formula 1 as follows:

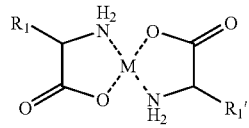

where $R_1$ and $R_1'$ are organic radicals, substituents or functional groups. $R_1$ and $R_1'$ can be the same or different.

In the above formula, the dashed lines can represent coordinate covalent bonds, covalent bonds, and/or ionic bonds. Further, when $R_1$ is H, the chelating agent is glycine, an amino acid that is the simplest of the α-amino acids. $R_1$, however, can represent any other side chain. Where the chelating agent is one of the naturally occurring α-amino acids, the $R_1$ side chains have been described as aliphatic which includes but is not limited to alanine, glycine, isoleucine, leucine, proline, and valine; aromatic which includes but is not limited to phenylalanine, tryptophan, tyrosine; acidic which includes but is not limited to aspartic acid, and glutamic acid; basic which includes but is not limited to arginine, histidine, and lysine; hydroxylic which includes but is not limited to serine, and threonine; sulfur-containing which includes but is not limited to cysteine, and methionine; amidic (containing amide group) which includes but is not limited to asparagine, and glutamine. $R_1$ could also be representative of any other side chain resulting in any of the non-natural occurring amino acids. Many of the amino acids have the same configuration for the positioning of the carboxylic acid oxygens and the α-amino nitrogen with respect to the metal ion. In other words, the chelate ring can be defined by the same atoms in each instance, even though the $R_1$ side chain group may vary. In some embodiments, amino acids with non-nucleophilic R groups include alanine, glycine, histidine, isoleucine, leucine, methionine, phenylalanine, serine, tryptophan, and valine.

The term "chelate ring" as used herein means the atoms of the ligand and central metal which form a heterocyclic ring with the metal as the closing member. In the interaction between the central metal and a multidentate ligand, one or more chelate rings of from 3 to 8 members can exist. The chelate ring can be of from 5 to 6 members.

The term "ligand" as used herein means a molecular group that is associated with a central metal atom. The ligand can be any ligand capable of forming a chelate with a metal. The terms monodentate, bidentate (or didentate), tridentate, tetradentate, and multidentate are used to indicate the number of potential binding sites of the ligand. For example, a carboxylic acid can be a bidentate or other multidentate ligand because it has at least two binding sites, the carboxyl oxygen and hydroxyl oxygen. An amino acid can have at least two binding sites and many amino acids will have multiple binding sites including the amino nitrogen and the carboxyl oxygen and hydroxyl oxygen atoms of a carboxylic acid functional group. When the side chain of the amino acid has one or more heteroatoms, the side chain may also present additional binding sites.

Examples of ligands include those with primary or secondary amines and more preferred ligands are those with primary amines. Other examples of ligands are those with primary or secondary amines and a carboxylic acid, each of which is α to a common carbon atom. Ligands can include those with primary and/or secondary amines. Ligands can include amino acids with primary amines. Ligands can also include primary or secondary amines each with a carboxylic acid β to the primary or secondary amine. Representative ligands include but are not limited to the α-amino acids which include the selected from the naturally occurring amino acids commonly found in biological structures including alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In some examples, the amino acid ligands may be selected from alanine, glycine, histidine, isoleucine, leucine, methionine, phenylalanine, serine, tryptophan, and valine. Other ligands include the amino acids 4-hydroxyproline, 5-hydroxylysine, homoserine, homocysteine, ornithine, β-alanine, γ-aminobutyric acid (GABA), statine, ornithine, and statin. In other embodiments, the amino acid is selected from the non-natural amino acids. In some embodiments, the amino acid is selected from the aliphatic naturally occurring amino acids selected from alanine, glycine, isoleucine, leucine, proline, and valine. Amino acids ligands can be the L-amino acids, the D-amino acids, or a racemic mixture. In some embodiments, the amino acids are the L-amino acids.

The term "metal" as used herein means any alkaline, alkaline earth, transition, and rare earth, basic, and semi-metals which can coordinate with a ligand. Metal can include nutritional minerals. Representative metals include the transition, lanthanide, and actinide metals. In some embodiments, the metal has d-orbitals capable of interacting with a ligand. In some embodiments, metals are selected from boron, calcium, chromium, cobalt, copper, iron, magnesium, manganese, molybdenum, potassium, selenium, vanadium, and zinc.

The term "nutritionally acceptable metal" as used herein means metals that are known to be needed by living organisms, particularly plants and mammals, including humans. Metals such as boron, calcium, chromium, cobalt, copper, iron, magnesium, manganese, potassium, selenium, vanadium, and zinc, among others, are examples of nutritionally acceptable metals.

The term "polyligated" as used herein means 2 or more ligands associated or bound to a metal.

The terms "hydrate" or "n-hydrate" as used herein means a molecular entity with some degree of hydration, where n is an integer representing the number of waters of hydration, e.g., monohydrate, dihydrate, trihydrate, tetrahydrate, pentahydrate, hexahydrate, heptahydrate, octahydrate, nonahydrate, etc.

A metal atom can accept bonds over and above the oxidation state of the metal because of the nature of chelation. For example, at the α-amino group of an amino acid, the nitrogen contributes both lone-pair electrons used in the bonding to the metal. These electrons fill available spaces in the d-orbitals of the metal forming a coordinate covalent bond. Thus, a metal ion with a normal valence of +2 can be bonded by up to eight bonds when fully chelated. In this state, the unfilled orbitals in the metal can be satisfied by both bonding electrons from lone pair electrons as well as electrons from ionic species. The chelate can be completely satisfied by the bonding electrons and the charge on the metal atom (as well as on the overall molecule) can still be zero. As stated previously, it is possible that the metal ion be bonded to the carboxyl oxygen by either coordinate covalent bonds or ionic bonds. The metal ion, however, can also be bonded to the α-amino group by coordinate covalent bonds only.

Atomic absorption spectroscopy (often referred to as AA) is a technique for determining the concentration of a particular metal element in a sample. The technique typically makes use of a flame to atomize the sample, but other atomizers such as a graphite furnace are also used. Three steps are involved in turning a liquid sample into an atomic gas: (1) desolvation—the liquid solvent is evaporated, and the dry sample remains; (2) vaporization—the solid sample vaporizes to a gas; (3) volatilization—the compounds making up the sample are broken into free atoms. A beam of light passes through a flame at its longest axis (the lateral axis) and hits a detector. The light that is focused into the flame is produced by a light source. Inside the light source is a cylindrical metal cathode containing the metal for excitation, and an anode. When a high voltage is applied across the anode and cathode, the metal atoms in the cathode are excited into producing light with a certain emission spectra. The type of hollow cathode tube depends on the metal being analyzed. For analyzing the concentration of copper in an ore, a copper cathode tube would be used, and likewise for any other metal being analyzed. The electrons of the atoms in the flame can be promoted to higher orbitals for an instant by absorbing a set quantity of energy (a quantum). This amount of energy is specific to a particular electron transition in a particular element. As the quantity of energy put into the flame is known, and the quantity remaining at the other side (at the detector) can be measured, it is possible to calculate how many of these transitions took place, and thus get a signal that is proportional to the concentration of the element being measured.

Inductively coupled plasma (ICP) is a type of plasma source in which the supplied energy comes from electrical currents produced by electromagnetic induction—by time-varying magnetic fields. Inductively coupled plasma atomic emission spectroscopy (ICP-AES), also referred to as inductively coupled plasma optical emission spectrometry (ICP-OES), is a type of emission spectroscopy that uses plasma to produced excited atoms that emit electromagnetic radiation at a wavelength characteristic of a particular element. Atoms in the plasma emit light (photons) with characteristic wavelengths for each element. This light is recorded by one or more optical spectrometers and when calibrated against standards the technique provides a quantitative analysis of the original sample. The intensity of the emission corresponds with the concentration of the element within a sample. The ICP-OES technique can be used to study the amount of a metal present in a sample. Inductively coupled plasma mass spectrometry (ICP-MS) is a type of mass spectrometry that is highly sensitive and capable of the determination of a range of metals and several non-metals at low concentrations. It is based on use of an inductively coupled plasma as a method of producing ions (ionization) coupled with a mass spectrometer as a method of separating and detecting the ions. ICP-MS can also be used to monitor isotopic speciation for the ions of choice. An ion-selective electrode (ISE) is a transducer (sensor) which converts the activity of a specific ion dissolved in a solution into an electrical potential which can be measured by a voltmeter or pH meter. The voltage is theoretically dependent on the logarithm of the ionic activity, according to the Nernst equation. The sensing part of the electrode is usually made as an ion-specific membrane, along with a reference electrode. Ion-selective electrodes can be used, where measurements of ionic concentration in an aqueous solution are required, including on a real time basis.

Determining the amount of unbound metal in the eluent may be accomplished by any of the various techniques known in the art for identifying and/or quantitating the amount of a substance in a sample. For example, the amount of unbound metal in the eluent may be determined using a spectroscopic method. In other embodiments, the amount of unbound metal in the eluent may be determined using a non-spectroscopic method. Suitable methods may include, for example, such techniques as atomic absorption spectroscopy (AA), inductively coupled plasma techniques (including ICP-AES, ICP-OES, and ICP-MS) ISE, titrations, conductivity, UV-Vis, fluorescence detection, PDA (photo diode array) or mass spectroscopy. A variety of other techniques are well-known to those skilled in the art and may also be used to detect a metal or metals present in a sample.

The techniques described herein may be used to assure quality control for the production of a variety of metal ligand complexes including amino acid chelates. The techniques include examination of samples with metal ligand complexes using ICP spectroscopy. Furthermore, larger proteinaceous amino acids and ligands may be characterized in the same manner as the simpler amino acid samples. Proteinaceous amino acids share an identical backbone which can participate in the chelate formation, namely an amine moiety in the alpha position relative to the carboxyl moiety.

Liquid Carriers

Samples can be suspended in liquid carriers for loading, eluting, and spectroscopically analyzing samples. Liquid carriers can include solvents which are free or substantially free of the metal or metals being investigated. Examples of suitable solvents include water and dimethylsulfoxide (DMSO).

In some embodiments, the liquid carrier includes a buffer solution. In other embodiments, the liquid carrier consists entirely of a buffer solution.

Buffer Solutions

Samples can be suspended in and loaded on to chromatography columns and eluted with aqueous buffer solutions. Multiple buffers can be used to obtain eluent fractions. For example, a first buffer can be used to charge the column, a second buffer can be used to elute bound metal (chelated metal with ligand), and a third buffer can be used to elute unbound metal (non-chelated form of metal). Various buffer systems may be selected and used that are compatible with the purification and detection system selected, in accordance with principles well-known to those skilled in the art. For example, suitable buffers that are compatible with HPLC systems may include, but are not limited to, NaCOOH, $Na_2SO_4$, $NH_4COOH$, $(NH_4)_2SO_4$, $MgSO_4$ and $Mg(COOH)_2$. Potassium salt buffers may also be used, including, for example, $K_2SO_4$, KCOOH.

pH

Chelation of a metal with a ligand can be affected by pH. In other words, accurate measurements should be obtained without changing the equilibrium of bound and unbound metal. Accordingly, when suspending the chelate product in a liquid carrier, the pH should be relatively compatible with the chelate produce. Otherwise an assessing the amount of unbound metal present in a sample could be distorted.

The general pH ranges that should be used should be compatible with the pH of the products being analyzed. For example, a pH range may be selected that is based on a speciation diagram. The ranges will vary based on the metals and ligands used. Also, the pH of the samples cannot be too high in some circumstances as precipitation will occur. However, this will depend greatly on the metal to ligand ratios as well as the concentration of the sample solution. Those skilled in the field of such chelate systems will be able to determine appropriate pH ranges for the samples.

Ion Chromatography

Column chromatography may be used to separate the bound metal-ligand chelate from unbound metal. Column chromatography is a separation technique in which the stationary bed can be placed in a tube. The particles of solid stationary phase (or support) may fill the entire volume or portion of the column. The solid phase may then be coated with a liquid mobile phase. The stationary phase may have an affinity for one or more of the constituents of a sample so that the relative rate of movement of the constituents through the stationary phase results in their separation.

An ion exchange column may be used to separate unbound metal from a metal-ligand chelate mixture. Ion exchange chromatography can utilize an ion exchange mechanism to separate analyte. It can be performed in columns or in a planar mode. Generally, the charged stationary phase separates charged compounds. An ion exchange column may include an ion exchange resin that itself includes charged functional groups which interact with oppositely charged groups of an analyte or analytes to be retained in the column.

Suitable columns may include strong cation exchange resins, such as styrene divinyl benzene as the base material with sulfite residues attached. The sulfite residue act as the active site for binding metals. This specific packing material can be utilized in gravimetric, planar (TLC), SPE (solid phase extraction) or HPLC columns. Similar exchange resins containing a functional group with either specific or non-specific affinity for a metal or groups of metals can be used.

Separation Techniques

The separation column is first charged using appropriate ions with a first buffer. The first buffer includes high ionic strength and neutral pH (e.g., 500 mM/pH 7). The charging ions are cations from a chosen buffer system. Second, the column is equilibrated with a second buffer which has a low ionic strength and a neutral pH (e.g., 5 mM/pH 7). The equilibration step not only washes excess unbound ions out of the column system, but it also prepares the column for sample application at neutral pH. Third, a sample is applied to the column. Once the sample has been loaded on the column, it is then eluted with the second buffer (the one used in the equilibration step). Again, this washes (or elutes) from the column any metal that is bound to ligand, and therefore not bound to the column. While the second buffer is being pushed (or gravimetrically pulled) through the column, the metal ions not bound to ligand interact (or associate) with the column. The first fraction to elute from a column, therefore, contains only the metal bound to ligand. After any metal bound to ligand is eluted, a third buffer is applied to the column. This buffer has a high ionic strength and a low pH, (500 mM/pH 2-3), both of which increase the systematic eluting strength washing off the metal remaining on the column.

Determining Amount of Metal

The amount of metal present in the eluent can be characterized using a variety of detection and quantitation techniques. Examples of detection techniques include atomic absorption spectroscopy (AA), inductively coupled plasma techniques (including ICP-AES, ICP-OES, and ICP-MS) ISE, titrations, conductivity, UV-Vis, fluorescence detection, PDA (photo diode array) or mass spectroscopy. A variety of other techniques may also be used to detect a metal or metals present in a sample, so long as they can characterize the amount of a metal or metal present in a sample.

EXAMPLES

Six buffer systems were prepared and evaluated: NaCOOH, $Na_2SO_4$, $NH_4COOH$, $(NH_4)_2SO_4$, $MgSO_4$ and $Mg(COOH)_2$. Three buffers were prepared for each system. Monovalent buffers were prepared in the following manner: buffer 1 was made at a pH of 7 with an ionic strength of 500 mM for the cation concentration. Buffer 2 was prepared at a pH of 7 with an ionic strength of 10 mM for the cation concentration. Buffer 3 was prepared at a pH of 3 with an ionic strength of 500 mM cation concentration.

The magnesium (Mg) buffers were prepared at half the ionic strength of the $Na^{+1}$ and $NH4^{+1}$ buffer systems. The pH of the buffers was the same. The concentration was halved to match the total cation charge present in the monovalent systems.

Both analyte samples and controls were prepared at 0.05 M concentrations. The copper EDTA (Cu EDTA) sample was prepared with a metal to ligand molar ratio of 1:1. The glycine control was prepared as a 0.10 M concentration of glycine with no pH adjustment.

The samples for the metal to ligand molar ratio evaluation were adjusted to a pH of 7 with 1 N NaOH, although the copper glycinate sample was prepared with a molar ratio of 1:1 metal to ligand adjusted to a pH of 5 because a precipitate forms above a pH of approximately 5.35.

Samples were separated by ion chromatography. The cation exchange columns used were Oasis 6 cc MCX LP extraction columns available from Waters Corporation. All eluent fractions were then quantitatively analyzed by ICP-OES for metal content and qualitatively analyzed by HPLC for ligand content followed by ninhydrin color indication used a secondary confirmation (see co-pending application Ser. No. 11/575,465, published as WO 2006/034195).

Control samples were also examined using Cu EDTA (100% bound metal chelate control), $CuSO_4$ (100% unbound metal control), and free ligand (ligand control to ensure ligand did not bind to the column).

Samples were loaded on to chromatography columns and eluted with buffer solutions. Three buffers were used to obtain eluent fractions. A first buffer was used to charge the column. A second buffer was used to elute bound metal (chelated metal with ligand). A third buffer was used to elute unbound metal (non-chelated form of metal). Ligand was eluted into the first fraction, monitored and confirmed by either ninhydrin or HPLC analysis. Elution of bound and unbound metal followed. Elution fractions were collected for metal analysis.

A separate column was used for each sample. The column was initially charged with 15 mL of buffer 1. The column was then equilibrated with 10 mL of buffer 2, followed by sample loading using 0.5 mL of sample. The bound metal was eluted into two fractions with buffer 2—10 mL and 5 mL fractions, labeled fraction 1 and fraction 2, respectively. The unbound metal was eluted into a single fraction with 10 mL of buffer 3 labeled fraction 3.

In one set of experiments, different buffers systems were evaluated. The buffers were chosen to evaluate if the procedure was robust and repeatable with differing anions and cations. Magnesium buffers were chosen to evaluate any differences between monovalent and divalent cation exchange as compared against sodium and ammonium buffers. In each buffer system experiment, the metal to ligand molar ratio was evaluated, as well as the effect of pH on a 1:2 copper to glycine molar ratio. Overall, two monovalent cations, a divalent cation, a monovalent anion, and a divalent anion were evaluated.

TABLE I

% Bound Copper

% Bound Cu

| | pH | $(NH_4)_2SO_4$ | $NH_4COOH$ | $Na_2SO_4$ | $NaCOOH$ | $MgSO_4$ | $Mg(COOH)_2$ |
|---|---|---|---|---|---|---|---|
| M:L trial set | | | | | | | |
| Cu Gly (1:4) | 7 | 93.60% | 92.33% | 84.88% | 96.10% | 76.88% | 100.00% |
| Cu Gly (1:3) | 7 | 92.00% | 90.62% | 83.69% | 92.80% | 76.55% | 96.90% |
| Cu Gly (1:2) | 7 | 78.60% | 76.48% | 81.12% | 82.00% | 66.97% | 94.40% |
| Cu Gly (1:1) | 5 | 33.50% | 36.63% | 24.87% | 36.80% | 25.08% | 55.80% |
| pH trial set | | | | | | | |
| Cu Gly (1:2) | 10 | 81.59% | 76.28% | 74.86% | 92.10% | 76.64% | 96.70% |
| Cu Gly (1:2) | 7 | 80.46% | 76.66% | 71.89% | 90.00% | 75.52% | 94.10% |
| Cu Gly (1:2) | 5 | 73.80% | 67.83% | 65.21% | 72.50% | 56.33% | 83.30% |
| Cu Gly (1:2) | 3 | 15.93% | 13.16% | 5.55% | 13.70% | 21.30% | 35.30% |
| Control set | | | | | | | |
| Glycine | n/a | 0.00% | 0.00% | 0.00% | 0.00% | 0.00% | 0.00% |
| $CuSO_4$ | n/a | 0.00% | 0.00% | 0.00% | 0.00% | 3.45% | 8.60% |
| Cu EDTA | 7 | 100.00% | 99.68% | 97.99% | 100.00% | 99.65% | 99.30% |

TABLE II

Statistical comparisons

| | | | All buffer systems | | | Monovalent anion buffer systems | | |
|---|---|---|---|---|---|---|---|---|
| | Samples | pH | Average | Std. Dev. | rsd | Average | Std. Dev. | Rsd |
| M:L | Cu Gly (1:4) | 7 | 90.63% | 0.084 | 9.25% | 91.73% | 0.0482 | 5.26% |
| | Cu Gly (1:3) | 7 | 88.76% | 0.074 | 8.30% | 89.78% | 0.0416 | 4.63% |
| | Cu Gly (1:2) | 7 | 79.93% | 0.089 | 11.14% | 79.55% | 0.0250 | 3.15% |
| | Cu Gly (1:1) | 5 | 35.45% | 0.113 | 31.93% | 32.95% | 0.0560 | 16.98% |
| pH | Cu Gly (1:2) | 10 | 83.03% | 0.092 | 11.10% | 81.21% | 0.0782 | 9.63% |
| | Cu Gly (1:2) | 7 | 81.44% | 0.088 | 10.76% | 79.75% | 0.0768 | 9.63% |
| | Cu Gly (1:2) | 5 | 69.83% | 0.091 | 13.00% | 69.84% | 0.0401 | 5.74% |
| | Cu Gly (1:2) | 3 | 17.49% | 0.101 | 57.74% | 12.08% | 0.0452 | 37.40% |
| Controls | Glycine | n/a | 0.00% | 0.000 | | 0.00% | 0.0000 | 0.00% |
| | CuSO4 | n/a | 2.01% | 0.035 | 174.84% | 0.00% | 0.0000 | 0.00% |
| | Cu EDTA | 7 | 99.44% | 0.008 | 0.76% | 99.42% | 0.0096 | 0.97% |

The experimental results, shown in Tables I & II, indicate that the solvent buffer systems were robust as between differing monovalent solvent systems. (See Table 1 and 2.) With each monovalent buffer set, free glycine eluted in only the first fraction. This was observed among the control samples as well.

The divalent buffer systems, however, behaved differently. Higher than expected bound copper was found than was calculated when eluted with divalent buffer systems. Also, $Cu^{+2}$ was present in fraction 2 of the $CuSO_4$ control suggesting that $Mg^{+2}$ caused coelution of $Cu^{+2}$ ions prematurely, which would result in an exaggerated measurement of the amount of copper-glycine chelate present in a sample.

Divalent buffer systems will also be expected to be useful in reducing the eluting strength (ionic strength), i.e., a less concentrated buffer set, or by using a longer ion chromatography column. The column capacity and the buffer strength could, therefore, affect the retention of the analyte cations. The valence of the buffer system cation in comparison to the analyte metal appears to affect the retention of the analyte metal on the column.

In another experiment, the effect of pH on the techniques was examined. 1 L of 0.05 M copper glycinate at a molar ratio of 1:2 was titrated with 2N NaOH from an initial pH of 3 to a final pH of 12, with data points at key intervals sampled and fractionated using a NaCOOH buffer system and tested for unbound $Cu^{+2}$ ions. More samples were examined at the inflection point where the rate of pH change was greatest to accurately analyze the concentration of unbound copper in solution. The behavior matched the behavior predicted by mathematical modeling.

We claim:

1. A method for assaying an amount of unbound metal in a liquid sample containing a metal-ligand chelate, comprising:
   contacting the sample with a liquid carrier;
   eluting the sample and liquid carrier through an ion chromatography column to produce an eluent;
   determining the amount of unbound metal in the eluent.

2. The method according to claim 1, wherein the amount of unbound metal in the eluent is determined by a spectroscopic method.

3. The method of claim 1, wherein the amount of unbound metal in the eluent is determined by a non-spectroscopic method.

4. The method of claim 1, wherein the amount of unbound metal in the eluent is determined by atomic absorption spectroscopy, inductively coupled plasma techniques, ISE, titrations, conductivity, UV-Vis, fluorescence detection, PDA (photo diode array) or mass spectroscopy.

5. The method according to claim 1, wherein the liquid carrier includes a buffer solution.

6. The method according to claim 1, wherein the liquid carrier has a pH of from about 2 to about 10.

7. The method according to claim 1, wherein the ion chromatography column includes a styrene divinyl benzene base material with sulfite residues.

8. A method for assaying an amount of unbound metal in a liquid sample suspected of containing a metal-ligand chelate, comprising:
   contacting the sample with a liquid carrier;
   eluting the sample and liquid carrier through an ion chromatography column to produce an eluent;
   determining the amount of unbound metal in the eluent;
   wherein the metal is selected from the group consisting of: boron, calcium, chromium, cobalt, copper, iron, magnesium, manganese, potassium, selenium, vanadium and zinc; and
   wherein the ligand is selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

9. The method according to claim 8, wherein the amount of unbound metal in the eluent is determined by a spectroscopic method.

10. The method of claim 8, wherein the amount of unbound metal in the eluent is determined by a non-spectroscopic method.

11. The method of claim 8, wherein the amount of unbound metal in the eluent is determined by atomic absorption spectroscopy, inductively coupled plasma techniques, ISE, titrations, conductivity, UV-Vis, fluorescence detection, PDA (photo diode array) or mass spectroscopy.

12. The method according to claim 8, wherein the liquid carrier includes a buffer solution.

13. The method according to claim 8, wherein the liquid carrier has a pH of from about 2 to about 10.

14. The method according to claim 8, wherein the metal is selected from boron and selenium.

15. The method according to claim 8, wherein the metal is selected from calcium and magnesium.

16. The method according to claim 8, wherein the metal is selected from chromium, cobalt, copper, iron, manganese, vanadium, and zinc.

17. The method according to claim 8, wherein the metal is selected from potassium.

* * * * *